United States Patent [19]
Avery et al.

[11] Patent Number: 6,041,910
[45] Date of Patent: Mar. 28, 2000

[54] BAGGAGE PUSHER DEVICE AND SYSTEM

[75] Inventors: Mark J. Avery, Farmington Hills; Wallace M. Catanach, III, Northville, both of Minn.

[73] Assignee: Jervis B. Webb Company, Farmington Hills, Mich.

[21] Appl. No.: 08/934,657

[22] Filed: Sep. 22, 1997

[51] Int. Cl.$^7$ .................................................. B65G 47/82
[52] U.S. Cl. ................................ 198/370.07; 198/370.08; 198/457.07; 198/598
[58] Field of Search ...................... 198/370.07, 370.08, 198/457.07, 598

[56] References Cited

U.S. PATENT DOCUMENTS

| | | |
|---|---|---|
| 3,045,801 | 7/1962 | Graybeal . |
| 4,256,216 | 3/1981 | Winters et al. . |
| 4,295,559 | 10/1981 | Neal et al. . |
| 4,441,604 | 4/1984 | Schlig et al. . |
| 4,564,105 | 1/1986 | Brouwer et al. . |
| 4,750,620 | 6/1988 | Braschos . |
| 5,010,998 | 4/1991 | MacMillan . |

FOREIGN PATENT DOCUMENTS 34 15 133 A1  10/1985  Germany .

OTHER PUBLICATIONS

Logan Glidepath Baggage Diverter Brochure, 1993.

Baldor AC Servco Control Catalog, pp. 1–1—1–7, 2–14—2–17, 1995.

Mark's Standard Handbook for Mechanical Engineers, 8$^{th}$ th ed., pp. 2–40, 1978.

Primary Examiner—Christopher P. Ellis
Assistant Examiner—Mark A. Deuble
Attorney, Agent, or Firm—Dickinson Wright PLLC

[57] ABSTRACT

A baggage pusher device for pushing baggage off a moving conveyor comprises a pusher cam with a pusher surface, a shaft supporting and rotating the pusher cam in a generally horizontal plane, a motor assembly and a frame to support at least the shaft. The pusher surface follows the Archimedes spiral function so that baggage contacting the pushing surface at any point therealong sees the same velocity. Control of the velocity assures that the baggage will not be damaged by high speed contact with the pushing device. The motor assembly utilizes a servo control with flux vector technology for quiet motor operation and smooth pusher device acceleration and deceleration.

11 Claims, 2 Drawing Sheets

BAGGAGE PUSHER DEVICE AND SYSTEM

FIELD OF THE INVENTION

The present invention is directed to a baggage pusher device, system and method of use, and in particular, to a device which utilizes a uniquely spiraled pushing surface to minimize or eliminate damage to the baggage during its pushing.

BACKGROUND ART

In the prior art, the use of baggage pushers to remove select pieces of baggage that travel along a conveyor are well known. U.S. Pat. No. 4,564,105 to Brouwer et al. discloses a tilted spiral article diverter having a spiral shaped sweep which is rotated to cause it to engage selected articles on a conveyor and push them off laterally. The sweep is supported on and rotated by a shaft which is inclined to the vertical and toward the conveyor whereby the circular path traced by its outer end is in an inclined plane. As it moves to its retracted position, the sweep moves upwardly. Since the free end of the sweep moves upwardly rather than laterally when the sweep is retracted, the total floor area occupied by the equipment is reduced without sacrificing the operating principles of the invention. This is an improvement over devices which occupy large areas in a conveyor system, such a luxury not available in certain industries, e.g., the airlines.

Brouwer et al., acknowledging a deficiency in the pusher design in catching or trapping soft sided baggage between the sweep and the conveyor, disclose a second embodiment wherein the shaft of the sweep is inclined both laterally towards the conveyor axis and towards an upstream direction of the conveyor, see FIGS. 7–10A and 13 thereof. In this embodiment, the face of the sweep is more to the side of the article rather than in front of it to reduce the tendency of the sweep to move over or trap any portion of the article between the sweep and the conveyor.

In either of the embodiments of the Brouwer et al. patent, there still remains a sizable gap between the sweep and the conveyor as a result of the inclined axis of the sweep shaft of rotation. This gap still provides the possibility of trapping or catching soft sided baggage during the sweep action. As a result, there exists a need for an improved baggage pusher which overcomes the drawbacks of the pusher disclosed in the Brouwer et al. patent.

High speed start-stop devices such as baggage pushers are often driven by motors utilizing clutch-brake mechanisms. These types of mechanisms are often noisy, require high maintenance and operate with discontinuous or jerky motions. Other types of baggage pushers, such as a Logan-Glidepath CamSort™ diverter made by Fabricom of Belgium, can strike a piece of baggage at a point on the pusher at a high velocity which can cause baggage damage. Accordingly, there exists a need for improved drives and designs for these types of devices.

In response to the drawbacks of prior art designs related to baggage pusher devices and the need for improved baggage pushers, the invention provides an improved baggage pusher device which overcomes the problems associated with prior art designs. The inventive pusher minimizes trapping of soft sided baggage, provides a low maintenance, quiet and smoothly operating drive and minimizes damage to baggage due to high velocity contact by the pusher device.

SUMMARY OF THE INVENTION

Accordingly, it is a first object of the present invention to provide an improved baggage pusher device.

Another object of the present invention is to provide a system combining the inventive pusher device with a conveyor.

A still further object of the present invention is to provide a method of pushing baggage off a conveyor employing the inventive pusher device.

One other object of the present invention is to provide a pusher device which strikes baggage at a uniform velocity regardless of the point of contact between the baggage and a surface of the pusher device.

Other objects and advantages of the present invention will become apparent as a description thereof proceeds.

In satisfaction of the foregoing objects and advantages, the present invention provides a baggage pusher device comprising a frame and a pusher cam having a pushing surface. A pusher shaft supports the pusher cam, the shaft supported by the frame in an orientation so that the pusher cam rotates in a generally horizontal plane and the pusher surface is generally vertical during its sweep. A motor assembly drives the pusher cam via the pusher shaft for rotation thereof. The pusher surface is shaped between a leading edge and a trailing edge in a spiral following the Archimedes spiral function as measured from an axis of the pusher shaft. In other words, a velocity at the pusher surface based on rotation of the pusher surface by the pusher shaft is the same all along a length of the pusher surface. In this way, a piece of baggage is contacted by the pusher surface at the same velocity regardless of where along the pusher surface the piece of baggage makes contact. Thus, high velocity contact between the pusher surface and baggage and possible damage to the baggage by such contact is avoided.

The motor assembly preferably includes a servo control which utilizes flux vector technology to adjust the phase and current applied to the motor for maximum torque, minimum maintenance, quiet operation and smooth acceleration and deceleration.

The pusher cam includes a body portion having a hub, the hub including a through opening for the pusher shaft. The body portion comprises a peripheral plate, a first portion of the peripheral plate including the pushing surface and a remaining portion of the peripheral plate interconnecting the leading edge of the pushing surface to the hub. The pusher cam can be segmented with spokes emanating from the hub to the first portion of the peripheral plate.

The pusher device can be combined with any conveyor system adapted for transporting baggage between two or more points.

The method aspect of the invention involves the steps of providing a plurality of pieces of baggage traveling along a conveyor. The inventive pusher device is arranged so that the pusher cam can sweep across the conveyor upper surface and divert one or more pieces of baggage to a collector chute or other form of transport or collection, e.g., another conveyor. When given the appropriate signal, the motor assembly is actuated to rotate the pusher shaft so that the pusher surface contacts the piece of baggage and pushes the piece off the conveyor. Because of the Archimedes spiral design of the pusher surface, contact between the piece of baggage and any point along the pusher surface occurs at the same velocity, i.e., the velocity of the rotating pusher surface.

The signal to the motor assembly for its actuation can be based on a predetermined condition(s), an operator tending the pusher device, a sensed condition upstream of the conveyor location where the pusher device is situated or any other known or contemplated schemes for controlling the flow of baggage along the conveyor. As part of the method, the pusher device can include the features discussed above with respect to the pusher cam and frame design.

BRIEF DESCRIPTION OF THE DRAWINGS

Reference is now made to the drawings of the invention wherein.

DESCRIPTION OF THE PREFERRED EMBODIMENTS

Figure 1:
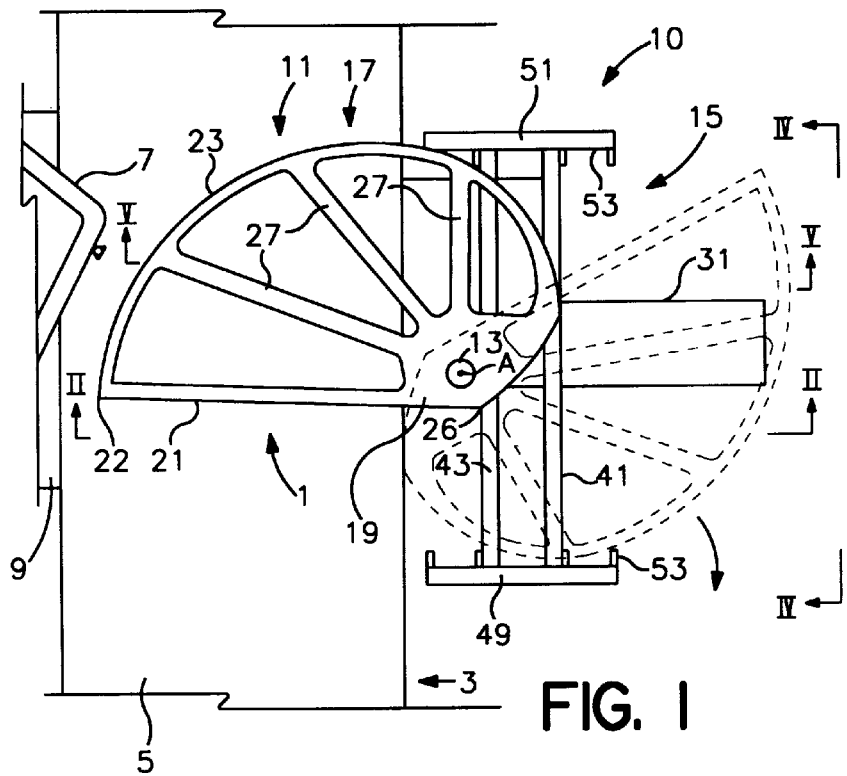
FIG. 1 is a plan view of one embodiment of the inventive baggage pusher device.

The inventive pusher device is especially adapted for diverting or pushing articles such as luggage, cargo, baggage or the like with minimal or no damage to the pushed article. Hereinafter, any article adaptable to be pushed with the inventive device will be referred to as baggage or a piece(s) of baggage. The inventive pusher employs a pushing surface that follows the Archimedes spiral, and therefore, is able to contact a piece of baggage at any point along the pusher surface at generally the same velocity. Since the velocity along the spirally shaped pushing surface does not substantially vary when pushing baggage, the device rotation can be controlled so that the pusher surface moves at a safe velocity, i.e., one that will not damage the baggage.

A preferred embodiment of the invention as a conveyor and pusher device system is depicted in FIGS. 1–5 as reference numeral 10 and includes a pusher device 1 in combination with a conveyor system 3 having a conveyor 5 as a part thereof. The system 1 is designed to divert or push a piece of baggage 7 onto a collecting device, e.g., a chute or conveyor, designated by the reference numeral 9.

The pusher device 1 comprises a pusher cam 11 which is mounted on a shaft 13. The cam 11 and shaft 13 are supported by a frame 15 comprising channels, angles and a plate as described hereinafter.

Figure 2:
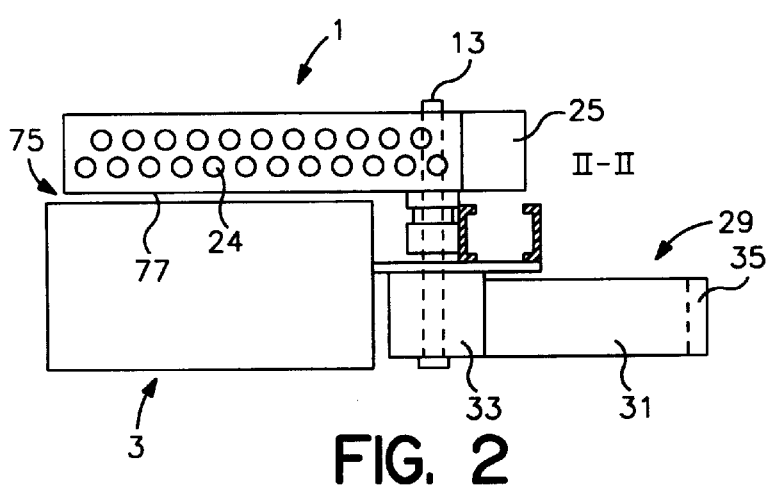
FIG. 2 is a sectional view taken along the line II—II of FIG. 1.

The cam 11 has a hub 19 having an opening for the shaft 13. The cam 11 also has a peripheral plate portion 21 extending from the hub to the leading edge 22. The portion 21 can include perforations 24 therein as depicted in FIG. 2.

Another peripheral plate portion extends from the leading edge 22 in a spiral shape to the trailing edge 26. A plurality of spokes 27 are disposed between the peripheral plate portion 23 and the hub 19. Although three spokes are shown, more or less spokes can be utilized if so desired. The pusher cam configuration is exemplary and other designs can be utilized providing that the Archimedes spiral pushing surface is retained.

The peripheral plate portion 23 is spiral in shape and has a pusher surface 25. The pusher surface 25 follows the Archimedes spiral function. More specifically, the Archimedes spiral function states that an ever-increasing ray when rotated at a uniform velocity will move at a point on the ray at a uniform velocity away from the center of rotation, i.e., the axis A of the shaft 13, see FIG. 1. The key to the spiral function is the uniform velocity which is directed across the conveyor belt 5. This uniform velocity provides a soft and gentle push of the baggage off the conveyor belt. No matter where the baggage strikes the pusher surface 23, the velocity will be the same, thus ensuring the gentle push mentioned above. Determination of the proper velocity or speed at which the pusher cam passes over the conveyor is a function of the conveyor width, size of the cam, the number of pieces of baggage traveling along the conveyor and the like. The speed determination is deemed within the skill of the art and is not believed to be necessary for understanding of the invention.

Figure 6:
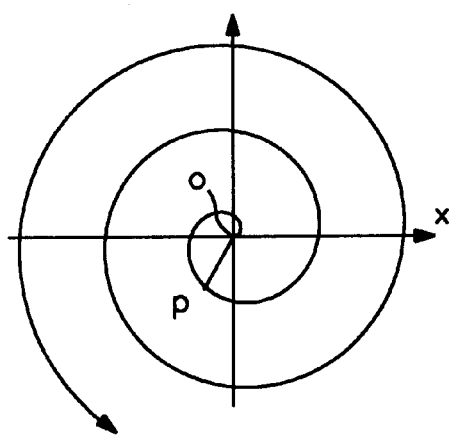
FIG. 6 depicts a spiral following the Archimedes spiral function.

Constructing the pusher surface with the Archimedes spiral follows the mathematical analysis below. Referring to FIG. 6, the spiral of Archimedes is traced by a point P which, starting from the axis A of the support shaft, represented by "O" in FIG. 6, moves with uniform velocity along the ray OP, while the ray OP itself revolves with uniform angular velocity about O. Using known polar equation coordinates $r=k$ rad $\theta$ or $r=a(\theta°/360°)$, for the Archimedes function, $a=2\pi k$, or $a=$ the distance, measured along a radius, from each coil to the next. In order to construct the spiral curve which is followed by the pusher surface 25, radii $O_1$, $O_2$, $O_3$, . . . are drawn making angles $1/n(360°)$, $2/n(360°)$, $3/n(360°)$, . . . with $O_x$, and along these radii, distances are laid off equal to $1/n(a)$, $2/n(a)$, $3/n(a)$, . . . ; the points thus reached will lie on the spiral. Further detail of the spiral of Archimedes can be found in Marks' Standard Handbook for Mechanical Engineers, Eighth Edition, Analytical Geometry, page 2–40, herein incorporated by reference in its entirety. Knowing how the Archimedes spiral is calculated, the pusher cam 11 can be fabricated so that the pusher surface 25 follows the Archimedes spiral as measured from the axis A of the support shaft 13.

Referring again to FIGS. 1 and 2, the pusher device 1 includes a motor assembly 29 for rotating the shaft 13 and controlling the speed, acceleration and deceleration of the pusher cam 11. The assembly 29 has a motor 31 including a servo control represented by 35 and a reducer/cone drive 33. The servo control is the type using flux vector technology. This technology is a closed loop control scheme using an algorithm to adjust the phase of voltage and current applied to a three-phase permanent magnetic synchronous motor. The servo control separates the current into its flux and torque producing components. They are independently adjusted and vectorially added to maintain a 90° relationship between them. This produces maximum torque from base speed down to and including zero speed. Above base speed, the flux component is reduced for constant horsepower operation. A preferred type of servo control is manufactured by Baldor® Electric Company of Fort Smith, Ariz. A preferred model is a Baldor Series 23H PWM servo control. Of course, other servo controls utilizing the flux vector technology can be utilized with the inventive device.

The servo control using the flux vector technology is designed to eliminate the problems with conventional clutch-brake force controls which require high maintenance, are noisy and involve sudden or jerky movements during motor operation.

The reducer/cone drive 33 is considered to be a conventional-type drive which links the motor output shaft (not shown) to the shaft 13 for rotation thereof. Since these type of drives are conventional in nature, a further description thereof is not deemed necessary for understanding of the invention. In addition, the reducer/cone drive 33 is exemplary, and any other type device linking the motor to the shaft can be used. The motor is preferably one of the Baldor BSM 90/100A series brushless servo motors or an equivalent thereof. The Baldor motors have continuous stall torque ratings ranging from 40 to 300 lb-in.

The frame 15 of the pusher device 1 is constructed of various channels, angles and other structural components for support of the motor assembly 29 and the shaft 13.

Figure 5:
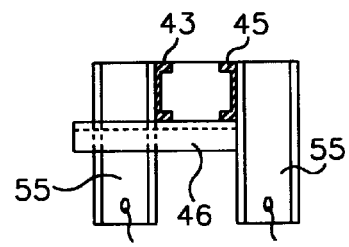
FIG. 5 is a sectional view of the frame of the inventive device taken along the line V—V of FIG. 1.
Figure 3:
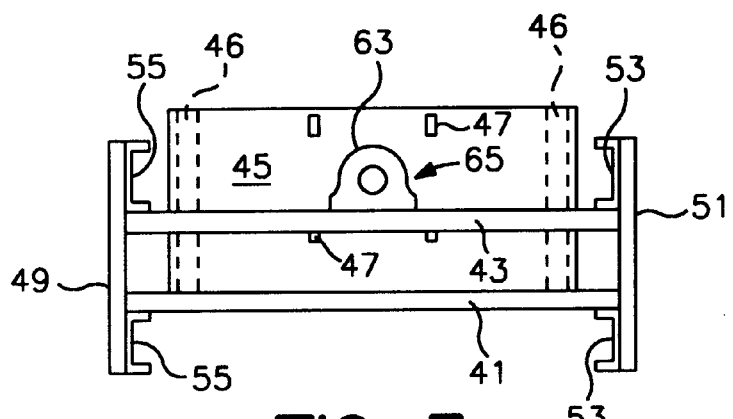
FIG. 3 is a plan view of the frame of the baggage pusher device.
Figure 4:
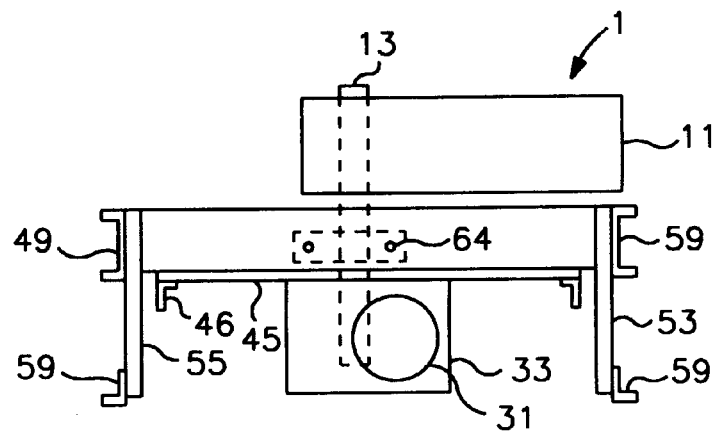
FIG. 4 is a side view along the line IV—IV of FIG. 1.

Referring now to FIGS. 3, 4 and 5, the frame 15 includes cross channels 41 and 43 and plate 45. The plate 45, with angles 46, is used for structural rigidity of the frame and for support of the reducer/cone drive 33 and cross channels 41 and 43. Plate 45 includes openings 47 to facilitate attachment to the housing of the reducer/cone drive 33.

Disposed at opposite ends of the cross channels 41 and 43 are horizontal end channels 49 and 51. The end channels lend support to the channel leg pairs 53 and 55, see FIG. 5 in particular.

The channel leg pairs 53 and 55 have openings 57 therethrough to facilitate attachment to wedge anchors 59, see FIG. 4. The wedge anchors 59 can then attach to a mounting surface to maintain the device 1 in a fixed position during its operation.

The cross channel 43 has a bearing assembly 63 fastened thereto, see FIG. 3. The assembly 63 has a bearing housing 65 with a bearing (not shown) therein to facilitate shaft support and rotation. The remaining parts of the shaft 13 which interface with the hub 19 and reducer/cone drive 33 are deemed conventional and require no further explanation for the understanding of the invention.

The plate, channels and angles can be welded or mechanically fastened together depending on the manner in which the various components interface. In certain instances, it may be preferred to weld adjacent channels together and in other instances use fasteners. For example, the reducer/cone drive 33 is linked to the plate by fasteners so that it can be easily removed and reinstalled for repair and/or maintenance. Similarly, the bearing housing 63 is attached by fasteners 64 to the cross channel 43 for repair and maintenance, see FIG. 4.

The frame 15 is an exemplary embodiment and other structures can be employed to position the pusher cam 11 in proximity to the conveyor 5 for the pushing of the pieces of baggage.

Referring to FIG. 1, the pusher cam 11 moves in a horizontal plane from an inoperative position as shown in cross hatch to an operative position. Since the pusher cam 11 is orientated in the horizontal plane, the clearance 75, see FIG. 2, between the conveyor 5 and the lower face 77 of the cam 11 is minimal. Thus, there is a minute likelihood that a portion of baggage, particularly soft-sided baggage, will wedge in the clearance 75 and be caught rather than pushed off the conveyor 5.

The control scheme for operating the baggage pushing device can be any type capable of actuating the motor assembly for pusher cam rotation given a pre-determined signal, manual operation or an operation using sensors to detect one or more pieces of baggage that should be pushed off the conveyor. Since these types of control schemes are well known in the art, a description thereof is not deemed necessary for understanding of the invention.

The pusher cam 11 is preferably made with a one-piece construction so that the hub 19 is integrally formed with the spokes 27 and peripheral plate portions 21 and 23. If desired, the pusher surface 25 could be padded with a resilient or other type of soft material to further lessen the impact on a piece of baggage when being diverted by the device.

The frame 15, shaft 13 and pusher cam 11 are preferably made durable materials of construction such as steel, aluminum or the like to withstand the pusher device's numerous cycles of operation.

As such, an invention has been disclosed in terms of preferred embodiments thereof which fulfill each and every one of the objects of the present invention as set forth above and provides a new and improved baggage pusher device, system and method of use.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. A baggage pusher device comprising:
   a) a frame;
   b) a pusher cam having a pushing surface;
   c) a pusher shaft supporting the pusher cam and being supported by the frame in an orientation so that the pusher cam rotates in a generally horizontal plane with the pusher surface being generally vertical; and
   d) a motor assembly connected to the pusher shaft for rotation thereof, the motor assembly comprising a motor, a reducer linking the motor to the pusher shaft and a servo control for the motor that separates current applied to the motor from a power source into flux and torque producing components;
   e) the pusher surface being shaped between a leading edge and a trailing edge in a spiral following the Archimedes spiral function as measured from an axis of the pusher shaft so that the pusher surface moves outwardly along a radial line extending from the pusher shaft at a constant velocity when the pusher shaft is rotated at a constant velocity.

2. The device of claim 1, wherein the pusher cam includes a body portion having a hub, the hub including a through opening for the pusher shaft, the body portion comprising a peripheral plate, a first portion of the peripheral plate including the pushing surface and a remaining portion of the peripheral plate interconnecting the leading edge of the pushing surface to the hub.

3. The device of claim 2, wherein the hub and body portion are integrally formed as one piece.

4. The device of claim 2, wherein the first portion of the peripheral plate is linked to the hub by a plurality of spokes.

5. A baggage pusher system comprising a conveyor and the baggage pusher device of claim 1 arranged adjacent the conveyor to push baggage off the conveyor.

6. A baggage pusher device comprising:
   a) a frame;
   b) a pusher cam having a pushing surface;
   c) a pusher shaft supporting the pusher cam and being supported by the frame in an orientation so that the pusher cam rotates in a generally horizontal plane with the pusher surface being generally vertical; and
   d) a motor assembly connected to the pusher shaft for rotation thereof;
   e) the pusher surface being shaped between a leading edge and a trailing edge in a spiral following the Archimedes spiral function as measured from an axis of the pusher shaft so that at the pusher surface moves outwardly along a radial line extending from the pusher shaft at a constant velocity when the pusher shaft is rotated at a constant velocity, the motor assembly comprising a motor, a reducer linking the motor to the pusher shaft and a servo control for the motor, the servo control separating current applied to the motor from a power source into flux and torque producing components to provide controlled acceleration and deceleration of the pusher surface.

7. The device of claim 6, wherein the pusher cam includes a body portion having a hub, the hub including a through opening for the pusher shaft, the body portion comprising a peripheral plate, a first portion of the peripheral plate including the pushing surface and a remaining portion of the peripheral plate interconnecting the leading edge of the pushing surface to the hub.

8. The device of claim 7, wherein the hub and body portion are integrally formed as one piece.

9. The device of claim 7, wherein the first portion of the peripheral plate is linked to the hub by a plurality of spokes.

10. The device of claim 7, wherein the remaining portion is perforated.

11. A baggage pusher device comprising:

a) a frame;

b) a pusher cam having a pushing surface;

c) a pusher shaft supporting the pusher cam and being supported by the frame in an orientation so that the pusher cam rotates in a generally horizontal plane with the pusher surface being generally vertical; and d) a motor assembly connected to the pusher shaft for rotation thereof;

e) the pusher surface being shaped between a leading edge and a trailing edge in a spiral following the Archimedes spiral function as measured from an axis of the pusher shaft so that the pusher surface moves outwardly along a radial line extending from the pusher shaft at a constant velocity when the pusher shaft is rotated at a constant velocity, wherein the pusher cam includes a body portion having a hub, the hub including a through opening for the pusher shaft, the body portion comprising a peripheral plate, a first portion of the peripheral plate including the pushing surface and a remaining portion of the peripheral plate interconnecting the leading edge of the pushing surface to the hub, wherein the remaining portion is perforated.

* * * * *

UNITED STATES PATENT AND TRADEMARK OFFICE
CERTIFICATE OF CORRECTION

PATENT NO. : 6,041,910
DATED : March 28, 2000
INVENTOR(S) : Mark J. AVERY & Wallace M. CATANACH, III It is certified that error appears in the above-identified patent and that said Letters Patent is hereby corrected as shown below:

Title page, Item [75],

Change the inventors' state of residence from Minnesota to Michigan.

Signed and Sealed this

Twenty-seventh Day of February, 2001

Attest:

NICHOLAS P. GODICI

Attesting Officer

Acting Director of the United States Patent and Trademark Office